United States Patent [19]

Ikeda et al.

[11] Patent Number: 4,849,424

[45] Date of Patent: Jul. 18, 1989

[54] PYRIMIDINE DERIVATIVES

[75] Inventors: Masazumi Ikeda, Toyonaka; Susumu Okabe, Kyoto, both of Japan

[73] Assignee: Nissin Shokuhin Kabushiki Kaisha, Osaka, Japan

[21] Appl. No.: 82,056

[22] Filed: Aug. 5, 1987

[30] Foreign Application Priority Data

Aug. 5, 1986 [JP] Japan ................... 61-184484

[51] Int. Cl.$^4$ .................. A61K 31/505; C07D 403/04
[52] U.S. Cl. .................... 514/256; 514/269; 514/272; 514/273; 514/274; 514/275; 544/317; 544/316; 544/319; 544/320; 544/321; 544/324; 544/328; 544/331
[58] Field of Search .............. 544/317, 319, 321, 328, 544/333, 316; 514/269, 273, 275

[56] References Cited

U.S. PATENT DOCUMENTS 3,040,047  6/1962  Sirakawa ..................... 544/331
3,647,814  3/1972  Greenfield ................... 544/331
3,914,223  10/1975  Seidel et al. ................ 544/331

FOREIGN PATENT DOCUMENTS 42-19593  10/1942  Japan .
54-115384  9/1979  Japan .

Primary Examiner—John M. Ford
Attorney, Agent, or Firm—Marshall, O'Toole, Gerstein, Murray & Bicknell

[57] ABSTRACT

The present invention relates to novel pyrimidine derivatives of the general formula

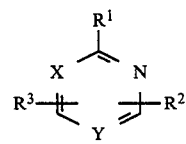

wherein $R^1$ represents a pyrazolyl, imidazolyl, or triazolyl group, $R^2$ represents hydrogen atom or lower alkyl group, $R^3$ represents a halo, amino, lower alkoxy, pyrazolyl, imidazolyl, triazolyl, piperidinyl, or aryloxy group, one of X or Y represents N and the other of X or Y represents CH, and the salts thereof.

These derivatives may be used in the treatment of peptic ulcer disease.

13 Claims, No Drawings

PYRIMIDINE DERIVATIVES

BACKGROUND

The present invention relates to novel pyrimidine derivatives having anti-peptic ulcer activities, to processes for preparing them, pharmaceutical compositions comprising them, and to their therapeutic use.

Various pyrimidine derivatives having pyrazolyl, imidazolyl, or triazolyl groups, are reported to be pharmacologically active, for example, as analgesics (Japanese Patent No. 42-19593) or as antibacterial agents (Japanese Patent No. 54-115384). Among these derivatives, none is reported as having anti-peptic ulcer activity.

SUMMARY OF THE INVENTION

Compounds according to the present invention include pyrimidine derivatives of the general formula

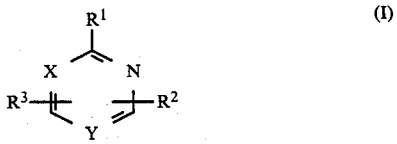

(I)

wherein $R^1$ represents a pyrazolyl, imidazolyl, or triazolyl group, $R^2$ represents a hydrogen atom or lower alkyl group, $R^3$ represents a halo, amino, lower alkoxy, pyrazolyl, imidazolyl, triazolyl, piperidinyl, or aryloxy group, one of X or Y represents N and the other of X or Y represents CH, and the salts thereof.

Compounds of general formula (I) tend to form acid salts. Therefore, the present invention also includes the organic and inorganic acid addition salts of compounds of formula (I). Examples of these salts are inorganic acid salts such as salts of hydrochloric acid, hydrobromic acid, sulfuric acid, and phosphoric acid, and organic acid such as salts of formic acid, acetic acid, maleic acid, tartaric acid, and p-toluenesulfonic acid. Salts which are pharmaceutically acceptable are preferred for use in compositions according to the present invention.

The compounds provided by the present invention are not described in the prior literature. They have an excellent protective effect on the ethanol-induced gastric mucosal damage model of the rat, and are useful as anti-ulcer agents in the treatment of animals, including humans. Pharmaceutical compositions of the invention comprise a compound of the general formula (I) or a pharmaceutically acceptable salt thereof in combination with a pharamceutically acceptable diluent, adjuvant or carrier. Treatment methods according to the invention comprise administering to a patient suffering from ulcers an antiulcer effective amount of a compound according to general formula (I) or a pharmaceutically acceptable salt thereof.

In the present specification and the appended claims, the term "lower", which qualifies groups or compounds, means that the group or compounds so qualified have not more than 6 carbon atoms. "Lower alkyl groups" referred to in the present application may be linear, branched or cyclic and include, for example, methyl, ethyl, n-propyl, isopropyl, n-butyl, isobutyl, n-pentyl, n-hexyl, cyclopropyl, cyclopentyl, and cyclohexyl groups. The term "lower alkyloxy groups" includes, for example, methoxy, ethoxy, n-propoxy, isopropoxy, n-butoxy, n-pentoxy, and n-hexoxy groups.

The term "aryloxy groups" includes, for example, phenoxy, tolyoxy, xyloxy, and naphtoxy groups.

In presently preferred compounds of the invention, pyrazolyl, imidazolyl, and triazolyl groups are linked to pyridine through a nitrogen atom of the substituent and thus the preferred compounds are designated as 1-pyrazolyl, 1-imidazolyl, and 1-triazolyl substituted pyridines.

Typical examples of compounds of formula (I) are listed below or described in the Examples.
4,6-Bis(1-pyrazolyl)pyrimidine
4,6-Bis(1-imidazolyl)pyrimidine
2,4-Bis(1-pyrazolyl)pyrimidine
2,4-Bis(1-imidazolyl)pyrimidine
6-Chloro-4-(1-pyrazolyl)pyrimidine
4-Methoxy-6-methyl-2-(1-pyrazolyl)pyrimidine
2-(1-Imidazolyl)-4-methoxy-6-methylpyrimidine
4-Methoxy-6-methyl-2-(1,2,4-triazol-1-yl)-pyrimidine
2-Methoxy-6-methyl-4-(1,2,4-triazol-1-yl)-pyrimidine
4-Ethoxy-2-(1-imidazolyl)-6-methylpyrimidine
4-Ethoxy-6-methyl-2-(1-pyrazolyl)pyrimidine
6-Chloro-4-(1-imidazolyl)pyrimidine
2-Chloro-4-(1-imidazolyl)pyrimidine
4-Chloro-2-(1-imidazolyl)pyrimidine
6-Methoxy-4-(1-pyrazolyl)pyrimidine
4-(1-Imidazolyl)-6-methoxypyrimidine
6-Isopropoxy-4-(1-pyrazolyl)pyrimidine
2-(1-Imidazolyl)-4-methoxypyrimidine
6-Piperidino-4-(1-pyrazolyl)pyrimidine
6-Amino-4-(1-pyrazolyl)pyrimidine
6-Phenoxy-4-(1-pyrazolyl)pyrimidine

DETAILED DESCRIPTION

The compounds of formula (I) and their salts may be produced by the following processes.

Procedure A:
Aromatic-substitution of a compound of formula (II) and its salts,

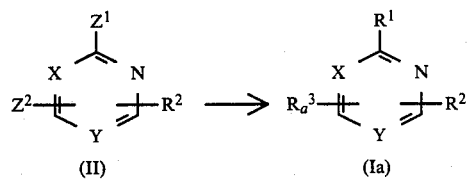

wherein $R^1$, $R^2$, X and Y are as described above with respect to formula (I), and $Z^1$ and $Z^2$ are the same or different and represent leaving groups such as halide residues, including chloro or bromo groups, or a tosyloxy group with pyrazole, imidazole, or triazole to provide compounds of formula (Ia) wherein $R^1$ and $R_a^3$ are the same.

In use of this reaction scheme for obtaining a compound in which the $R^1$ and $R_a^3$ substituents are the same, the pyrazole, imidazole or triazole may be used in an amount of at least 2 equivalents, preferably 2 to 10 equivalents, and more preferably 2 to 5 equivalents per mole of the starting compound (II). The reaction is usually carried out in a suitable organic solvent including, for example, anhydrous tetrahydrofuran, anhydrous ether, anhydrous dioxane, benzene, toluene, dimethylsulfoxide, acetonitrile, dimethylformamide, pyridine, and the like. It is preferred that these solvents do not contain water in the presence of a base such as sodium hydride, potassium hydride, sodium metal, potassium metal, or n-butyl lithium. The base may be used in an amount of at least 1 equivalent, preferably 1 to 5 equivalents, and more preferably 1 to 1.5 equivalents per mole of the starting compound (II).

The reaction may be carried out at any suitable temperature, but preferably is carried out at room temperature.

Procedure B:

Aromatic-substitution of a compound of formula (III) and its salts

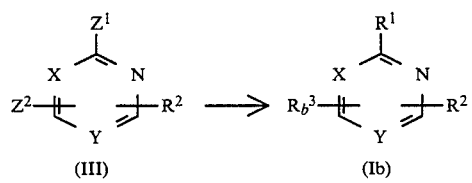

wherein $R^1$, $R^2$, X and Y are as described with respect to formula (I), $Z^1$ and $Z^2$ are the same or different and represent halogen leaving groups such as chloro or bromo groups, with pyrazole, imidazole, or triazole to provide compounds of the formula (Ib) wherein $R_b{}^3$ represents a halogen group such as chloro or bromo groups.

In use of this reaction scheme for obtaining a halogen-containing compound of formula (Ib), dihalogenated pyrimidine derivatives (III) are reacted with 1 equivalent of pyrazole, imidazole, or triazole according to the same procedures as described with respect to the reactions of Procedure A.

The reaction may be carried out by the same procedure described with respect to Procedure A.

Procedure C:

Aromatic-substitution of a compound of formula (IV) and its salts

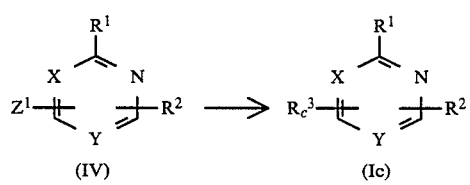

wherein $R^1$, $R^2$, X and Y are as described with respect to formula (I), and $Z^1$ represents a leaving group such as a halide residue, including chloro or bromo groups, or a tosyloxy group, with a selected lower alkyl alcohol or aryl alcohol to provide compounds of formula (Ic) wherein $R_c{}^3$ is a lower alkoxy or aryloxy group.

In use of this reaction scheme for obtaining a compound of formula (Ic) from a compound of formula (IV), the reaction may be carried out through use of the appropriate lower alkyl alcohol or aryl alcohol in the presence of a base, or by the action of the corresponding lower alkoxy-metal or ayloxy-metal. Examples of suitable bases include 1,5-diazabicyclo-(5,4,0)-5-undecane, or 1,5-diazabicyclo-(3,4,0)-5-nonene, and the like.

The reaction may be carried out in the presence of a solvent such as benzene, toluene, dimethylsulfoxide, acetonitrile, pyridine, or alcohols at room temperature or with heating.

Alternatively, a compound of formula (Ic) may be obtained using the scheme of Procedure B followed by the scheme of Procedure C. Moreover, a dihalogenated compound of formula (III) may be preliminarily treated to replace one of the halogen groups with the desired lower alkoxy or aryloxy group and the resulting compound may be treated according to the general type of reaction involved in Procedure B to effect the substitution of a pyrazolyl, imidazolyl or triazolyl group for the remaining halo substituent.

Procedure D:

Aromatic-substitution of a compound of formula (V) and its salts

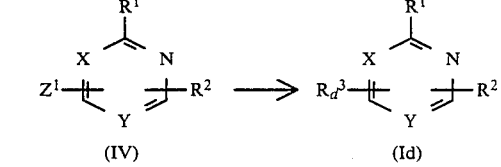

wherein $R^1$, $R^2$, X and Y are as described with respect to formula (IV) and $Z^1$ represents a leaving group such as a halide residue, including chloro or bromo groups, or a tosyloxy group, with ammonia, pyrazole, imidazole, triazole or piperidine to provide compounds of formula (Id) wherein $R_d{}^3$ represents an amino, pyrazolyl, imidazolyl, triazolyl, or piperidinyl group.

In use of this reaction scheme for obtaining a compound of formula (Id) having an amino, a 1-pyrazolyl, a 1-imidazolyl, a 1-triazolyl, or a 1-piperidinyl group, from a compound of formula (V), the reaction may be carried out by reacting ammonia or the selected amine compound in the absence of a solvent under heating, or in the presence of a base such as sodium hydride or sodium amide in a solvent such as benzene, toluene, methanol, ethanol, pyridine, or water at room temperature or with heating. Advantageously, by using excess amount of amines, such as ammonia, the reaction may be carried out in a solvent in the absence of a base.

Compounds according to the invention are preferably administered by an oral route but may also be administered topically, parenterally, or by suppository. The compounds may be used in the form of a base or as a physiologically acceptable salt. In general, the compounds are associated with a pharmaceutically acceptable carrier or diluent to provide a pharmaceutical composition.

In the case of oral administration, it is convenient to use the medical compositions of this invention in the form of capsules or tablets, but the compositions may also be used in the form of sustained release preparations. Furthermore, the compositions may be used in the form of sugar-coated preparations or syrups.

A conventional daily oral dose is 10 mg to 1000 mg per day, in the form of dosage units consisting of about 2 mg to 200 mg per dosage unit. A convenient regimen in the case of a slow release tablet is two or three times a day. Parenteral administration may be by injections at intervals or as a continuous infusion. Injection solutions may contain from 1 to 100 mg/ml of active ingredient.

Compounds of this invention possess worthwhile therapeutic properties, cytoprotective effects, low toxicity, and other advantageous properties.

The present invention is illustrated in greater detail by the following Examples. Examples 1 through 23 are descriptive of synthesis of compounds according to the present invention. Example 24 illustrates the cytoprotective effect of several compounds according to the present invention. In Example 25, the anti-stress ulcer activity of a compound according to the present invention is set forth. Example 26 relates to tests revealing the low toxicity of compounds according to the present invention.

EXAMPLE 1

4,6-Bis(1-pyrazolyl)pyrimidine

In 4 ml of anhydrous tetrahydrofuran, 160 mg of sodium hydride (60% in mineral oil) was dissolved washed with n-pentane, and 272 mg of pyrazole in 6 ml of anhydrous tetrahydrofuran was dripped into the mixture under cooling with ice in a stream of nitrogen. The mixture was stirred at room temperature for 20 minutes. To this mixture was added 298 mg of 4,6-dichloropyrimidine in 3 ml of anhydrous tetrahydrofuran under cooling with ice, and the mixture was stirred at room temperature for 12 hours. The solvent was distilled away under reduced pressure, and the residue was extracted with 20 ml of methylene chloride. The organic layer was washed with 5 ml of saturated sodium chloride solution, and dried over anhydrous sodium sulfate. The solvent was distilled away and the residue was purified by a silica gel column chromatography using a mixture of chloroform and methanol (30:1) to give an amorphous product. The product was recrystallized from n-hexane to provide 334 mg of 4,6-bis(1-pyrazolyl)pyrimidine acicular crystal having a melting point of 133°–133.5° C.

NMR(CDCl$_3$)δ: 6.57(1H,m), 7.88(2H,s), 8.47(1H,s), 8.67(2H,d,J=6 Hz), 8.87(1H,2).

EXAMPLE 2

4,6-Bis(1-imidazolyl)pyrimidine

In anhydrous tetrahydrofuran, 298 mg of 4,6-dichloropyrimidine was substituted with 272 mg of imidazole. The reaction mixture was treated according to the procedure of Example 1 to yield 294 mg of 4,6-bis(1-imidazoly)pyrimidine, recrystallized from a mixture of isopropyl-alcohol and methanol, and having a melting point of 243°–244° C.

NMR(CDCl$_3$)δ: 6.5(2H,m), 7.7(3H,m), 8.7(3H,m).

EXAMPLE 3

2,4-Bis(1-pyrazolyl)pyrimidine

In anhydrous tetrahydrofuran, 149 mg of 4,6-dichloropyrimidine was substituted with 136 mg of pyrazole. The reaction mixture was treated according to the procedure of Example 1 to yield 179 mg of 2,4-bis(1-pyrazolyl)pyrimidine, recrystallized from n-hexane, the compound had a melting point of 152°–153° C.

NMR(CDCl$_3$)δ: 6.5(2H,m), 7.8(3H,m), 8.65(3H,m).

EXAMPLE 4

2,4-Bis(1-imidazolyl)pyrimidine

In anhydrous tetrahydrofuran, 149 mg of 2,4-dichloropyrimidine was substituted with 136 mg of imidazole. The reaction mixture was treated according to the procedure of Example 1 to yield 163 mg of 2,4-bis(1-imidazolyl)pyrimidine, recrystallized from a mixture of n-hexane and ethyl acetate, the compound had a melting point of 131°–132° C.

NMR(CDCl$_3$)δ: 7.3(3H,m), 7.9(2H,m), 8.7(3H,m).

EXAMPLE 5

6-Chloro-4-(1-pyrazolyl)pyrimidine

In 2 ml of anhydrous tetrahydrofuran, 80 mg of sodium hydride (60% in mineral oil) was dissolved, washed with n-pentane, and 136 mg of pyrazole in 3 ml of anhydrous tetrahydrofuran was added dropwise under cooling with ice in a stream of nitrogen. The mixture was stirred at room temperature for 20 minutes. To this mixture was added 298 mg of 4,6-dichloropyrimidine in 3 ml of anhydrous tetrahydrofuran, and the mixture was stirred at room temperature for 12 hours. The solvent was distilled off under reduced pressure, and the residue was extracted with 20 ml of methylene chloride. The organic layer was washed with 5 ml of saturated sodium chloride solution, and dried over anhydrous sodium sulfate. The solvent was distilled away, and the residue was separated and purified by a silica gel column chromatography using a mixture of chloroform and methanol (30:1) to give an amorphous product. The product was recrystallized from n-hexane to provide 296 mg of 6-chloro-4-(1-pyrazolyl)pyrimidine, an acicular crystal having a melting point of 128°–129° C.

NMR(CDCl$_3$)δ: 6.5(1H,m), 7.77(1H,s), 7.93(1H,s), 8.53(1H,d,J=3 Hz), 8.73(1H,s).

EXAMPLE 6

4-Methoxy-6-methyl-2-(1-pyrazolyl)pyrimidine

In anhydrous tetrahydrofuran, 159 mg of 2-chloro-4-methoxy-6-methylpyrimidine was substituted with 68 mg of pyrazole. The reaction mixture was treated according to the procedure of Example 5 to yield 103 mg of 4-methoxy-6-methyl-2-(1-pyrazolyl)pyrimidine, and recrystallized from n-hexane to give a compound having a melting point of 52.5°–53° C.

NMR(CDCl$_3$)δ: 2.53(3H,s), 4.07(3H,s), 6.48(2H,bs), 7.85(1H,bs), 8.63(1H,d,J=3 Hz).

EXAMPLE 7

2-(1-Imidazolyl)-4-methoxy-6-methylpyrimidine

In anhydrous tetrahydrofuran, 159 mg of 2-chloro-4-methoxy-6-methylpyrimidine was substituted with 68 mg of imidazole. The reaction mixture was treated according to the Procedure of Example 5 to yield 97 mg of 2-(1-imidazolyl)-4-methoxy-6-methylpyrimidine, recrystallized from n-hexane, having a melting point of 53°–54° C.

NMR(CDCl$_3$)δ: 2.43(1H,s), 4.00(1H,s), 6.40(1H,s), 7.80(1H,bs), 8.53(1H,bs).

EXAMPLE 8

4-Methoxy-6-methyl-2-(1,2,4-triazol-1-yl)-pyrimidine

In anhydrous tetrahydrofuran, 159 mg of 2-chloro-4-methoxy-6-methylpyrimidine was substituted with 69 mg of 1,2,4-triazole. The reaction mixture was treated according to the procedure as in Example 5 to yield 92 mg of 4-methoxy-6-methyl-2-(1,2,4-triazol-1-yl)-pyrimidine, recrystallized from n-hexane, having a melting point of 142.5°–143° C.

NMR(CDCl$_3$)δ: 2.53(1H,s), 4.07(1H,s), 6.57(1H,s), 8.13(1H,s), 9.20(1H,s).

EXAMPLE 9

2-Methoxy-6-methyl-4-(1,2,4-triazol-1-yl)pyrimidine

In anhydrous tetrahydrofuran, 159 mg of 4-chloro-2-methoxy-6-methylpyrimidine was substituted with 69 mg of 1,2,4-triazole. The reaction mixture was treated according to the procedure of Example 5 to yield 43 mg of 2-methoxy-6-methyl-4-(1,2,4-triazol-1-yl)pyrimidine, recrystallized from n-hexane, having a melting point of 98°–98.5° C.

NMR(CDCl$_3$)$\delta$: 2.55(3H,s), 4.06(3H,s), 7.34(1H,s), 8.08(1H,s), 9.17(1H,s).

EXAMPLE 10

4-Ethoxy-2-(1-imidazolyl)-6-methylpyrimidine

In anhydrous tetrahydrofuran, 173 mg of 2-chloro-4-ethoxy-6-methylpyrimidine was substituted with 68 mg of imidazole. The reaction mixture was treated according to the procedure of Example 5 to yield 103 mg of 4-ethoxy-2-(1-imidazolyl)-6-methylpyrimidine, recrystallized from a mixture of n-hexane and ethyl acetate, having a melting point of 115.5°–116° C.

NMR(CDCl$_3$)$\delta$: 1.13(3H,t,J=8 Hz), 2.44(3H,s), 4.50(2H,q,J=8 Hz), 6.43(1H,s), 7.20(1H,s), 7.90(1H,s), 8.63(1H,s).

EXAMPLE 11

4-Ethoxy-6-methyl-2-(1-pyrazolyl)pyrimidine

In anhydrous tetrahydrofuran, 173 mg of 2-chloro-4-ethoxy-6-methylpyrimidine was substituted with 68 mg of pyrazole. The reaction mixture was treated according to the procedure of Example 5 to yield 110 mg of 4-ethoxy-6-methyl-2-(1-pyrazolyl)pyrimidine, an oily compound.

NMR(CDCl$_3$)$\delta$: 1.40(3H,t,J=7 Hz), 2.40(3H,s), 4.50(2H,q,J=7 Hz), 6.4-6.6(2H,m), b 7.81(1H,bs), 8.28(1H,d,J=3 Hz).

EXAMPLE 12

6-Chloro-4-(1-imidazolyl)pyrimidine

In anhydrous tetrahydrofuran, 298 mg of 4,6-dichloro-pyrimidine was substituted with 136 mg of imidazole. The reaction mixture was treated according to the procedure of Example 5 to yield 283 mg of the 6-chloro-4-(1-imidazolyl)pyrimidine, recrystallized from a mixture of n-hexane and ethyl acetate, having a melting point of 131.5°–132° C.

NMR(CDCl$_3$)$\delta$: 7.2-7.4(1H,m), 7.43(1H,s), 7.6-7.9(1H,m), 8.47(1H,s), 8.89(1H,s).

EXAMPLE 13

2-Chloro-4-(1-imidazolyl)pyrimidine

In anhydrous tetrahydrofuran, 680 mg of 2,4-dichloropyrimidine was substituted with 680 mg of imidazole. The reaction mixture was then treated according to the procedure of Example 5 to yield 840 mg of the 2-chloro-4-(1-imidazolyl)pyrimidine, recrystallized from a mixture of n-hexane and ethyl acetate, having a melting point of 127.5°–128° C.

NMR(CDCl$_3$)$\delta$: 7.22(1H,s), 7.26(1H,d,J=6 Hz), 7.7(1H,m), 8.42(1H,s), 8.69(1H,d,J=6 Hz).

EXAMPLE 14

4-Chloro-2-(1-imidazolyl)pyrimidine

In anhydrous tetrahydrofuran, 1500 mg of 2,4-dichloropyrimidine was substituted with 680 mg of imidazole. The reaction mixture was treated according to the procedure of Example 5 to yield 401 mg of 4-chloro-2-(1-imidazolyl)pyrimidine recrystallized from a mixture of n-hexane and ethyl acetate, having a melting point of 138°–139° C.

NMR(CDCl$_3$)$\delta$: 7.2(2H,m) 7.7(1H,m), 8.5(2H,m).

EXAMPLE 15

6-Methoxy-4-(1-pyrazolyl)pyrimidine

In 3 ml of anhydrous methanol, 23 mg of sodium metal was dissolved, and to the resulting solution, 180 mg of 6-chloro-4-(1-pyrazolyl)pyrimidine in 2 ml of anhydrous methanol was added dropwise with stirring at room temperature in a stream of nitrogen overnight. The solvent was distilled off under reduced pressure, and the residue was extracted with 20 ml of methylene chloride. The organic layer was washed with 5 ml of saturated sodium chloride solution, and dried over anhydrous sodium sulfate. The solvent was distilled away, and a residue was purified by a silica gel column chromatography using chloroform to give an amorphous product. The product was recrystallized from n-hexane to provide 132 mg of the plate crystal 6-methoxy-4-(1-pyrazolyl)pyrimidine having a melting point of 108.5°–109° C.

NMR(CDCl$_3$)$\delta$: 4.00(3H,m), 6.5(1H,m), 7.24(1H,s), 7.73(1H,bs), 8.51(1H,d,J=3 Hz), 8.57(1H,bs).

EXAMPLE 16

4-(1-Imidazolyl)-6-methoxypyrimidine

Following the procedure of Example 15, 180 mg of 6-chloro-4-(1-imidazolyl)pyrimidine was reacted with 23 mg of sodium metal and 2 ml of anhydrous methanol to yield 136 mg 4-(1-imidazolyl)-6-methoxypyrimidine, having a melting point of 152°–153° C., recrystallized from a mixture of n-hexane and ethyl acetate.

NMR(CDCl$_3$)$\delta$: 4.03(3H,s), 6.63(1H,s), 7.1-7.2(1H,m), 7.5-7.6(1H,m), 8.38(1H,s), 8.63(1H,s).

EXAMPLE 17

6-Isopropoxy-4-(1-pyrazolyl)pyrimidine

Following the procedure of Example 15, 180 mg of 6-chloro-4-(1-pyrazolyl)pyrimidine was reacted with 23 mg of sodium metal and 3 ml of anhydrous isopropylalcohol to yield 127 mg of an oily substance, 6-isopropoxy-4-(1-pyrazolyl)pyrimidine, NMR(CDCl$_3$)$\delta$: 1.32(3H,s), 1.43(3H,s), 5.40(1H,sept,J=6 Hz), 6.3-6.6(1H,s), 7.73(1H,s), 8.51(1H,d,J=3 Hz), 8.55(1H,s).

EXAMPLE 18

2-(1-Imidazolyl)-4-methoxypyrimidine

Following the procedure of Example 15, 180 mg of 4-chloro-2-(1-imidazolyl)pyrimidine were reacted with 23 mg of sodium metal and 2 ml of anhydrous methanol was carried out to yield 134 mg of 2-(1-imidazolyl)-4-methoxypyrimidine, having a melting point of 78°–79° C., recrystallized from a mixture of n-hexane and ethyl acetate.

NMR(CDCl$_3$)$\delta$: 4.05(3H,s), 6.65(1H,d,J=6 Hz), 7.2(1H,m), 7.9(1H,m), 8.37(1H,d,J=6 Hz), 8.61(1H,bs).

EXAMPLE 19

6-Piperidino-4-(1-pyrazolyl)pyrimidine

In a sealed tube, 180 mg of 6-chloro-4-(1-pyrazolyl)-pyridimine and 2.5 ml of piperidine were warmed at 140° C. for 30 hours. This reaction mixture was dissolved with methylene chloride, and washed with water. The organic fraction was dried over anhydrous sodium sulfate, and distilled off. The residue was purified by alumina column chromatography using a mixture of n-hexane and ethyl acetate (8:1) to yield 218 mg of oily 6-Piperidino-4-(1-pyrazolyl)pyrimidine.

NMR(CDCl$_3$)δ: 1.59(6H,bs), 3.63(4H,bs), 6.2–6.5(1H,m), 7.02(1H,s), 7.67(1H,bs), 8.38(1H,s), 8.49(1H,d,J=3 Hz).

EXAMPLE 20

6-Amino-4-(1-pyrazolyl)pyrimidine

In sealed tube, 180 mg of 6-chloro-4-(1-pyrazolyl)-pyrimidine and 2.5 ml of concentrated ammonium hydroxide were warmed at 140° C. for 30 hours. The reaction mixture was dissolved in methylene chloride, and washed with water. The organic fraction was dried over anhydrous sodium sulfute, and distilled off. A residue was recrystallized from methanol to yield 148 mg of 6-amino-4-(1-pyrazolyl)pyrimidine, a flaking crystal having a melting point of 236.5°–237° C., NMR(CDCl$_3$)δ: 6.57(1H,m), 7.2(2H,b), 7.53(1H,d,J=3 Hz), 8.38(1H,s), 8.53(1H,d,J=3 Hz).

EXAMPLE 21

6-Phenoxy-4-(1-pyrazolyl)pyrimidine

In 10 ml of benzene, 180 mg of 6-chloro-4-(1-pyrazolyl)pyrimidine, 175 ml of phenol, and 152 mg of 1,8-diazabicyclo-(5,4,0)-7-undecene (DBU) were dissolved, and refluxed for 7 hours. This reaction solution was washed with water, and an organic fraction was dried over anhydrous sodium sulfate. The resulting extract was distilled to give a residue, and the residue was purified by alumina gel column chromatography using a mixture of n-hexane and ethyl acetate (2:1) to yield 175 mg 6-phenoxy-4-(1-pyrazolyl)pyrimidine, recrystallized from n-hexane, to give an acicular crystal having a melting point of 92.5°–93.5° C., NMR(CDCl$_3$)δ: 6.4(1H,m), 7.3(6H,m), 7.70(1H,s), 8.50(1H,m), 8.53(1H,s).

EXAMPLE 22

Tablets

Tablets each comprising 50 mg or 100 mg of the active compound, may be prepared as follows:

| Prescription I (50 mg Tablet) | |
|---|---|
| 4,6-Bis(1-pyrazolyl)pyrimidine | 50 mg |
| Corn Starch | 40 mg |
| Lactose | 70 mg |
| Carboxymethyl Cellulose Calcium | 20 mg |
| Magnesium Stearate | 10 mg |
| Talc | 10 mg |
| Total | 200 mg |

Finely pulverized 4,6-bis(1-pyrazolyl)pyrimidine was mixed altogether with the corn starch, the purified lactose and the carboxymethyl cellulose calcium. This product was granulated by conventional process. The granules were mixed with talc and with magnesium stearate as a lubricant. The mixture was then processed to form tablets, each weighing 200 mg. The tablets comprised 50 mg of the active ingredient per tablet.

| Prescription II (100 mg Tablet) | |
|---|---|
| 4,6-Bis(1-pyrazolyl)pyrimidine | 100 mg |
| Corn Starch | 20 mg |
| Lactose | 40 mg |
| Carboxymethyl Cellulose Calcium | 20 mg |
| Magnesium Stearate | 10 mg |
| Talc | 10 mg |
| Total | 200 mg |

EXAMPLE 23

Capsules

| Prescription III | (50 mg Capsules) |
|---|---|
| 4,6-Bis(1-pyrazolyl)pyrimidine | 50 mg |
| Starch | 73 mg |
| Lactose | 70 mg |
| Magnesium Stearate | 7 mg |
| Total | 200 mg |

4,6-Bis(1-pyrazolyl)pyrimidine was finely pulverized, and starch, lactose and magnesium stearate were added to the pulverized product. The components were mixed well, and the mixture was filled into No. 5 capsules.

EXAMPLE 24

Male Sprague-Dawley rats (body weight: 220–240 g, 7 weeks) were deprived of food but allowed free access to water for 24 hours prior to the experiments. Each control and experimental group consisted of 3 rats. One hundred and fifty mM HCl-60% ethanol (v/v) was given p.o. in a volume of 1 ml/rat. The animals were sacrificed 1 hour later, and the stomach was removed and inflated by injecting 10 ml of 2% formalin to fix the inner and outer layers of the gastric walls. Subsequently, the stomach was incised along the greater curvature and washed gently with ice-cold saline.

Gastric lesions were identified in the grandular portion. The length of lesions was measured in millimeters (mm) under a dissecting microscope with a square grid (×10), and lesion severity was expressed as the total length of lesions per stomach.

Test compound (I) (10 mg/kg), suspended in 1% carboxymethyl cellulose (CMC), or 1% carboxymethyl cellulose for the control was orally administered 30 minutes before HCl-ethanol administration. The ulcer length of the treated group and the control group were compared and the inhibitory rates were calculated. Results were obtained as reported in Table I.

TABLE I

| Example No. | Compound | Inhibition (%) | ED50 (mg/kg) |
|---|---|---|---|
| 1 | 4,6-Bis(1-pyrazolyl)pyrimidine | 95.6 | 0.72 |
| 6 | 4-Methoxy-6-methyl-2-(1-pyrazolyl)pyrimidine | 87.2 | — |
| 7 | 2-(1-Imidazolyl-4-methoxy-6-methylpyrimidine | 82.6 | — |
| 9 | 2-Methoxy-6-methyl-4-(1,2,4-triazol-1-yl)pyrimidine | 75.7 | — |
| 10 | 4-Ethoxy-2-(1-imidazolyl)-6-methylpyrimidine | 80.7 | — |
| 11 | 4-Ethoxy-6-methyl-2-(1-pyrazolyl)pyrimidine | 78.3 | — |
| 15 | 6-Methoxy-4-(1-pyrazolyl)-pyrimidine | 95.6 | — |

TABLE I-continued

| Example No. | Compound | Inhibition (%) | ED50 (mg/kg) |
| --- | --- | --- | --- |
| 16 | 4-(1-Imidazolyl)-6-methoxy-pyrimidine | 91.3 | 5.6 |
| 17 | 6-Isopropoxy-4-(1-pyrazolyl)pyrimidine | 79.8 | — |
| 19 | 6-Piperidino-4-(1-pyrazolyl)-pyrimidine | 79.2 | — |
| 4 | 2,4-Bis(1-imidazolyl)pyrimidine | 78.2 | — |

EXAMPLE 25

Male Sprague-Dawley rats (body weight: 230–280 g) were placed under restraint in a stress cage after fasting for 15 hours, and immersed vertically in the water bath kept at 22° C. to the level of the xiphoid of the animal. After restraint-immersion for 7 hours the animals were killed, and the stomach from each animal was fixed with formalin.

Each stomach was opened by cutting along the greater curvature, and ulcer area (mm²) was measured with a stereoscopic microscope. Ulcer indices of the treated group and the control group were compared, and inhibitory rates were calculated. The tested compound, either 4,6-bis(1-pyrazolyl) pyrimidine (32 mg/kg) suspended in 0.1% methylcellulose (MC) or 0.1% methylcellulose (MC) alone, was orally administered 5 minutes before the restraint-immersion. The results appear in Table II.

TABLE II

| No. | $R^1$ | $R^2$ | $R^3$ | Inhibition (%) |
| --- | --- | --- | --- | --- |
| 1 | pyrazolyl | H | pyrazolyl | 73.6 |

EXAMPLE 26

A 0.3% CMC-Na suspension of a test compound was orally administered to groups of Slc:Wistar/KY rats (male: 90–120 g), each group consisting of 10 rats. The animals were observed for 72 hours. LD50 values were calculated by the Probit method to be as follows:

| (i) | LD50 value of 4,6-bis(1-pyrazolyl)-pyrimidine: | >3000 mg/kg |
| --- | --- | --- |
| (ii) | LD50 value of 4-(1-imidazolyl)-6-methoxypyrimidine: | 400 mg/kg |

It is understood that modifications and improvements will occur to those skilled in the art upon consideration of the present invention. Therefore, it is intended that all such modifications and improvements come within the scope of the invention as claimed.

What is claimed:
1. A pyrimidine derivative of the following formula:

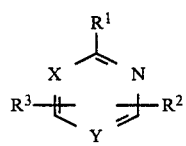

wherein $R^1$ represents an unsubstituted 1-pyrazolyl, 1-imidazolyl, or 1,2,4-triazol-1-yl group, $R^2$ represents a hydrogen atom or lower alkyl group, $R^3$ represents a halo, amino, lower alkoxy or an unsubstituted 1-pyrazolyl, 1-imidazolyl, 1,2,4-triazol-1-yl, piperidinyl, or phenoxy group, one of X or Y represents N, the other of X or Y represents CH, and the salts thereof, provided that where X is N and $R^1$ is 1-pyrazolyl, $R^3$ may not be halo, amino or lower alkoxy.

2. A compound as recited in claim 1 wherein the $R^2$ represents hydrogen atom or methyl group.

3. A compound as recited in claim 1 wherein the $R^1$ and $R^3$ are the same or different and represent an unsubstituted 1-pyrazolyl, 1-imidazolyl, or 1,2,4-triazol-1-yl group.

4. A compound as recited in claim 1 wherein the $R^3$ represents a methoxy, ethoxy, or isopropoxy group.

5. A compound as recited in claim 1 wherein the $R^3$ represents a chloro or bromo group.

6. A compound as recited in claim 1 which is
4,6-Bis(1-pyrazolyl)pyrimidine
4,6-Bis(1-imidazolyl)pyrimidine
2,4-Bis(1-pyrazolyl)pyrimidine
2,4-Bis(1-imidazolyl)pyrimidine
6-Chloro-4-(1-pyrazolyl)pyrimidine
2-(1-lmidazolyl)-4-methoxy-6-methylpyrimidine
4-Methoxy-6-methyl-2-(1,2,4-triazol-1-yl)-pyrimidine
2-Methoxy-6-methyl-4-(1,2,4-triazol-1-yl)-pyrimidine
4-Ethoxy-6-methyl-2-(1-pyrazolyl)pyrimidine
6-Chloro-4-(1-imidazolyl)pyrimidine
2-Chloro-4-(1-imidazolyl)pyrimidine
4-Chloro-2-(1-imidazolyl)pyrimidine
6-Methoxy-4-(1-pyrazolyl)pyrimidine
4-(1-Imidazolyl)-6-methoxypyrimidine
6-Isopropoxy-4-(1-pyrazolyl)pyrimidine
2-(1-Imidazolyl)-4-methoxypyrimidine
6-Piperidino-4-(1-pyrazolyl)pyrimidine
6-Amino-4-(1-pyrazolyl)pyrimidine
6-Phenoxy-4-(1-pyrazolyl)pyrimidine
or a pharmaceutically acceptable salt thereof.

7. An antiulcer composition comprising an antiulcer effective amount of a compound of the formula

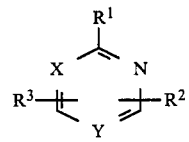

wherein $R^1$ represents an unsubstituted 1-pyrazolyl, 1-imidazolyl, or 1,2,4-triazol-1-yl group, $R^2$ represents a hydrogen atom or lower alkyl group, $R^3$ represents a halo, amino, lower alkoxy or an unsubstituted 1-pyrazolyl, 1-imidazolyl, 1,2,4-triazol-1-yl, piperidinyl, or phenoxy group, one of X or Y represents N, the other of X or Y represents CH, and the salts thereof.

8. A composition according to claim 7 wherein, in the compound, $R^2$ represents a hydrogen atom or methyl group.

9. A composition as recited in claim 7 wherein, in the compound, $R^1$ and $R^3$ are the same or different and represent an unsubstituted 1-pyrazol 1-imidazolyl, or 1,2,4-triazol-1-yl group.

10. A composition as recited in claim 7 wherein, in the compound, the $R^3$ represents a methoxy, ethoxy, or isopropoxy group.

11. A composition as recited in claim 7 wherein, in the compound, $R^3$ represents a chloro or bromo group.

12. A composition as recited in claim 7 wherein the compound is 4,6-Bis(1-pyrazolyl)pyrimidine
4,6-Bis(1-imidazolyl)pyrimidine
2,4-Bis(1-pyrazolyl)pyrimidine
2,4-Bis(1-imidazolyl)pyrimidine
6-Chloro-4-(1-pyrazolyl)pyrimidine
4-Methoxy-6-methyl-2-(1-pyrazolyl)pyrimidine
2-(1-Imidazolyl)-4-methoxy-6-methylpyrimidine
4-Methoxy-6-methyl-2-(1,2,4-triazol-1-yl)-pyrimidine
2-Methoxy-6-methyl-4-(1,2,4-triazol-1-yl)-pyrimidine
4-Ethoxy-2-(1-imidazolyl)-6-methylpyrimidine
4-Ethoxy-6-methoxy-2-(1-pyrazolyl)pyrimidine
6-Chloro-4-(1-imidazolyl)pyrimidine
2-Chloro-4-(1-imidazolyl)pyrimidine
4-Chloro-2-(1-imidazolyl)pyrimidine
6-Methoxy-4-(1-pyrazolyl)pyrimidine
4-(1-Imidazoly)-6-methoxypyrimidine
6-Isopropoxy-4-(1-pyrazolyl)pyrimidine
2-(1-Imidazolyl)-4-methoxypyrimidine
6-Piperidino-4-(1-pyrazolyl)pyrimidine
6-Amino-4-(1-pyrazolyl)pyrimidine
6-Phenoxy-4-(1-pyrazolyl)pyrimidine
or a pharmaceutically acceptable salt thereof.

13. A method for the treatment of ulcers which comprises administering to a patient suffering therefrom an antiulcer effective amount of a composition according to any one of claims 7, 8, 9, 10, 11 or 12.

* * * * *

UNITED STATES PATENT AND TRADEMARK OFFICE
CERTIFICATE OF CORRECTION

PATENT NO. : 4,849,424
DATED : July 18, 1989
INVENTOR(S) : IKEDA ET AL.

It is certified that error appears in the above-identified patent and that said Letters Patent is hereby corrected as shown below:

Col. 5, line 41, "(1-imidazoly)" should be
--(1-imidazolyl)--

Col. 7, line 37, "b" should be deleted.

Col. 10, line 61, "2-(1-Imidazolyl-4-methoxy-6-" should be
--2-(1-Imidazolyl)-4-methoxy-6- --

Col. 12, line 23, "2-(1-1midazolyl" should be
--2-(1-Imidazolyl--

Signed and Sealed this

Eighth Day of January, 1991

Attest:

HARRY F. MANBECK, JR.

*Attesting Officer*  *Commissioner of Patents and Trademarks*